Figure 1:
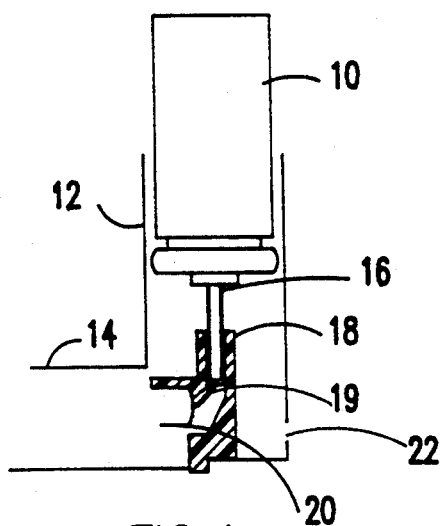

United States Patent [19]
Burns et al.

[11] Patent Number: 5,284,133
[45] Date of Patent: Feb. 8, 1994

[54] INHALATION DEVICE WITH A DOSE-TIMER, AN ACTUATOR MECHANISM, AND PATIENT COMPLIANCE MONITORING MEANS

[75] Inventors: James S. Burns, Darien, Conn.; Daniel R. Marshak, Cold Spring Harbor, N.Y.

[73] Assignee: Armstrong Pharmaceuticals, Inc., New Canaan, Conn.

[21] Appl. No.: 919,030

[22] Filed: Jul. 23, 1992

[51] Int. Cl.$^5$ .............. A61M 11/00; A61M 16/00; A62B 9/00; A62B 27/00; G08B 3/00
[52] U.S. Cl. .............. 128/200.23; 128/200.14; 128/200.24; 128/202.22; 128/203.14; 128/203.24; 128/203.15; 222/635; 222/649; 222/23
[58] Field of Search .............. 128/200.14–200.24, 128/202.22, 203.12–203.15, 419 G, 724, 203.24; 604/54, 239; 222/23, 36–38, 645, 644, 649, 635

[56] References Cited

U.S. PATENT DOCUMENTS

| | | | |
|---|---|---|---|
| 4,106,503 | 8/1978 | Rosenthal et al. | 128/203.12 |
| 4,291,688 | 9/1981 | Kistler | 128/200.14 |
| 4,677,975 | 7/1987 | Edgar et al. | 128/200.14 |
| 4,817,822 | 4/1989 | Rand et al. | 128/200.23 |
| 4,934,358 | 6/1990 | Nilsson et al. | 128/200.23 |
| 4,955,371 | 9/1990 | Zamba et al. | 128/200.23 |
| 5,020,527 | 6/1991 | Dessertine | 128/200.23 |
| 5,042,467 | 8/1991 | Foley | 128/200.14 |

FOREIGN PATENT DOCUMENTS

| | | | |
|---|---|---|---|
| 8605991 | 10/1986 | World Int. Prop. O. | 128/200.14 |
| 9106334 | 5/1991 | World Int. Prop. O. | 128/200.23 |

OTHER PUBLICATIONS

Matthew, Clinical Toxicology 8(5); pp. 495–513 (1975) (Abstract).
Miller et al., American Family Physician, vol. 40, No. 4, p. 175(9) (Oct. 1989) (Abstract).
Bird, Northwest Medicine, 69(8), p. 553 (1970) (Abstract).
Magness, Applied Therapeutics (Toronto), 7:649, 651, 653 (1965).
Salzman, Hospital and Community Psychiatry (Washington) 33:2, pp. 133–136 (Feb. 1982) (Abstract).
Milner, Medical Journal of Australia (Sydney) 2(3): pp. 153–155 (1969) (Abstract).
Spector, "Is Your Asthmatic Patient Really Complying?", Annals of Allergy, vol. 55, pp. 552–556 (Oct. 1985).
Mawhinney et al., "Compliance in clinical trials of two nonbronchodilator, antiasthma medications", Annals of Allergy, vol. 66, pp. 294–299 (Apr. 1991).

(List continued on next page.)

Primary Examiner—Edgar S. Burr
Assistant Examiner—Kimberly L. Asher
Attorney, Agent, or Firm—Whitham & Marhoefer

[57] ABSTRACT

An inhalation device is provided with a mechanism to assure patient compliance with a drug dosage regimen. The control mechanism includes a controller (24), a timer (26), an actuator (28) and a signalling device (30). The controller (24) is programmed or preset with a time and dosage schedule for the drug to be delivered. For example, the controller (24) may be programmed to allow for two puffs from an MDI every eight hours. The actuator (28) operates in conjunction with the timer (26) and prevents the inhalation device from being actuated after the programmed dosage has been administered at the prescribed interval. The actuator (28) could be an electronically controlled valve (58) or pawl (66) arrangement or other suitable mechanism. The signaling device (30) provides an audible, visual or tactile sensation during the time period prescribed for administration of the drug so that the patient is reminded to inhale his or her medicine at the prescribed time intervals. The history of actuation, non-actuation, and improper attempts at actuation can all be recorded and analyzed off-site at a later by a physician, pharmacist, or other authorized health care professional.

16 Claims, 3 Drawing Sheets

OTHER PUBLICATIONS

Nedelmann, Nervenarzt 53(1), pp. 33–38 (1982) (Abstract).

Kahl et al., Public Health Reports, vol. 107, No. 1, p. 37(11) (Jan.–Feb. 1992) (Abstract).

Morris et al., Comprehensive Psychiatry 15(6), pp. 537–547 (1974) (Abstract).

Witt, Dissertation Abstracts International 39(11), p. 5321-B (1979) (Abstract).

Beardsley, "Evaluation of a patient drug self administration program", (Ph.D. Dissertation), Dissertation Abstracts International, Univ. M, No. 789627, p. 208 (1977) (Abstract).

Venulet, International Journal of Clinical Pharmacology and Biopharmacy (Munchen), 15(4), pp. 151–154 (1977) (Abstract).

INHALATION DEVICE WITH A DOSE-TIMER, AN ACTUATOR MECHANISM, AND PATIENT COMPLIANCE MONITORING MEANS

CROSS-REFERENCE TO RELATED APPLICATIONS

This patent application is related to the copending U.S. Patent Application entitled "TARGETED SYSTEMIC DELIVERY OF MEDICATION VIA AEROSOL" having Ser. No. 07/884,799 which was filed May 19, 1992, and the contents of that patent application is herein incorporated by reference.

BACKGROUND OF THE INVENTION

1. Field of the Invention

The present invention generally relates to inhalation devices such as metered dose inhalers (MDIs), nebulizers, and dry powder inhalers. More particularly, the invention is directed to a dose or timing controlled actuator that operates in conjunction with an inhalation device to prevent both patient under-compliance with prescribed medication dosing and patient abuse of or dependence on prescribed medication. Specifically, the invention contemplates the use of an actuator to prevent patient actuation of the inhalation device at non-prescribed intervals or at higher than prescribed doses, and the use of an alarm to notify the patient regarding undercompliance/underdosing situations and attempted abuse situations.

2. Description of the Prior Art

Patient compliance with a doctor's instructions on prescribed medication is extremely important in the treatment of medical disorders. Although the rate of patient compliance is higher when he or she must return to the hospital or physician's office to receive the medication, most drug treatment regimens require the patient to administer the drugs at regular intervals without supervision by hospital personnel or the patient's physician or other qualified medical personnel. Obviously, the treatment of a medical disorder will be frustrated if the patient does not administer the drugs as prescribed. In the past, physicians have had to rely on the patient's self-interest in his or her own well being to assure that drugs are properly administered as scheduled.

With anti-anxiety or sedative/hypnotics, such as valium and barbiturates, it is widely recognized that there is a real possibility that the patient will abuse or become dependent on the drug. In *Clinical Toxicology* 8(5):495-513 (1975), it was argued that physicians should avoid the prescription of barbiturates because of the risk of dependence and the high toxicity of the drugs. Miller et al., *American Family Physician* v40, n4, p175(9) (October 1989), reported on the use of benzodiazepine drugs in the treatment of anxiety and particularly discussed the identification of dependence and addiction to these drugs. Bird, *Northwest Medicine* 69(8)533 (1970), reported on the problem of sedative overdose and suggested that sedatives should only be dispensed in small quantities and only on a restricted basis. Magnes, *Applied Therapeutics (Toronto)* 7:649 (1965) discussed the problems in the use of tranquilizing drugs in treating patients with psychoneuroses and demonstrated that in many patients treated with ethclorvynol an addiction develops.

Many drugs have a narrow therapeutic range and can have severe side effects. It is well recognized that controlling the dosing of these types of drugs is important in mitigating problems with side effects. Salzman, *Hospital and Community Psychiatry (Washington)* 33:2, 133-136 February 1982, reported that elderly patients are more susceptible to psychotropic drug toxicity, severe extrapyramidal side-effects from neuroleptics, and anticholinergic side-effects from tricyclic antidepressants. Milner, *Medical Journal of Australia (Sydney)* 2(3):153-155 (1969), reported that psychotropic drugs can have gastrointestinal side effects. Miller et al., *American Family Physician* v40, n4, p175(9) (October 1989), reported that benzodiazapine drugs pose adverse side effects to patients.

Many drugs can be extremely expensive (e.g., certain purified peptides and proteins). Controlling patient dosing of these drugs can have economic benefits.

An MDI typically comprises a canister under pressure fitted with a metering valve where the canister is filled with an aerosol formulation that includes a drug dissolved or dispersed in a propellant together with a surfactant. Nebulizers are devices which include mechanical or electronic devices (e.g., piezoelectric element) to atomize a drug suspension positioned in a containment cup. Nebulizers include an air or other gas source to deliver the atomized drug to the patient as a fine mist. Dry powder inhalers include mechanical or electronic devices to produce a fine mist from a powdered drug composition. MDIs, nebulizers, and dry powder inhalers have been used for many years to treat pulmonary disorders such as asthma. Examples of the types of drugs which have been routinely provided by these aerosolizing devices include: β-agonists such as albuterol (salbutamol), isoproterenol, ephedrine, epinephrine, salmeterol, terbutaline; corticosteroids such as triamcinolone acetonide, beclomethasone diproprionate, dexamethasone, and aldosterone; allergic mediators such as cromclyn sodium; antibiotics; and anticholinergics.

Patient non-compliance with inhalation devices has been recognized as a major medical problem. In 1985, Dr. Spector reported in Spector, "Is your Asthmatic Patient Really Complying?", *Annals of Allergy*, 55:552-556 (1985), that patient compliance using a nebulizer to deliver Iodoxamide, a cromolyn-like aerosol having a prophylactic (as opposed to immediate) bronchodilator effect, was extremely poor. In the investigation, patients were provided with a device called a Nebulizer Chronolog which contained a microswitch and timer that recorded the time of each use of the nebulizer. In addition, the patients were asked to record their use of the nebulizer in a diary. The patients were not told that the time of actuation of the nebulizer was also being automatically recorded. Over a several week study where Iodoxamide was to be delivered at prescribed hourly intervals, it was determined from the automatically recorded usage data that all patients underdosed themselves. The mean rate of underusage was 48% for the study and the highest rate of underusage was 95.6%. Nevertheless, many patients did not tell the truth about their underusage in their diaries.

In a later study, Mawhinney et al., "Compliance in clinical trials of two nonbronchodilator, antiasthma medications", *Annals of Allergy*, 66:294-299 (1991), two groups of patients were provided with MDIs that were insertable into Nebulizer Chronolog devices (reported to be available from the ATA Corporation of Denver, Colo.). One group received either Iodoxamide or placebo, while the other group received tixocortol pivalate or placebo. Even though patients were told they were being monitored, compliance was very low. Underusage was observed in a number of patients. In addition, overusage was observed in a number of patients, especially on days preceding follow up visits to the physicians office. In fact, only one patient in thirty four was found to be truly compliant.

There is a need to improve patient compliance with prescribed dosing schedules. As was reported in Nedelmann, *Nervenarzt* 53(1):33-38 (1982), it was reported that patient compliance with a doctor's drug prescription for psychotherapeutic drugs is only around 50%. Furthermore, Kahl et al., *Public Health Reports* Vol. v107, issue n1, page p37(110) (January-February 1992) reported that overuse, underuse and inappropriate use of drugs by elderly patients are common problems. Several different solutions have been proposed for helping improve patient compliance. For example, Morris et al., *Comprehensive Psychiatry* 15(6):537-547 (1974), suggested that overdoses with the widely prescribed psychotherapeutic drugs may be avoided if there was a requirement of including an emetic or some other agent as a deterrent in the drugs, Witt, *Dissertation Abstracts International* 39(11):5321-B (1979) discusses the use of post-discharge pill count measurements, Beardsley, (Ph.D Dissertation University of Minn. 1977) reports a study that demonstrated increased compliance with a patient's increased knowledge about drugs gained by close interaction with pharmacists, and Venulet, *Journal of Clinical Pharmacology and Biopharmacy (Munchen)* 15(4):151-154 (1977), notes that having doctors understand the personality and sociocultural background of patients will aid in compliance. This invention is particularly directed to an improved inhalation device which aids in assuring patient compliance.

There is also a need for an inhalation device which can provide some assurance that a patient is not circumventing a dosing schedule by not inhaling medication. Mawhinney et al., *Annals of Allergy*, 66:294-299 (1991), points out that the Nebulizer Chronolog has no mechanism to determine whether a patient has activated the MDI without inhaling medication or how often they might have done so. Mawhinney et al. particularly note that Fox, *Bull Int. Union Against Tuberculosis* 32:307-331 (1961), reports that the self-administration of medicaments was studied in depth and it was particularly noted that home health visitors frequently found supplies of unused medications in a patient's home, despite finding a correct number of pills in the containers presented to the health investigators. Hence, there is a tendency of some patient's to "cheat" on dosing schedules. Preventing a patient's ability to "cheat" would help ensure compliance with prescribed dosing schedules.

SUMMARY OF THE INVENTION

It is an object of this invention to provide a dose-timer and actuator mechanism for inhalation devices such as MDIs, nebulizers and dry powder inhalers, which promotes patient compliance.

It is another object of this invention to provide a dose-timer and actuator mechanism that prevents abuse of addictive drugs by preventing too many actuations at a prescribed intervals and preventing additional actuations at non-prescribed intervals.

It is another object of this invention to provide a dose-timer and actuator mechanism that helps promote the proper administration of drugs that are active within a narrow therapeutic range and helps control the dosing of expensive drugs.

It is another object of this invention to provide a dose-timer and actuator mechanism that helps reduce undercompliance to prescribed dosing schedules by signalling the patient during an interval when a dose is to be taken, if the patient has not inhaled his or her medication.

It is yet another object of this invention to provide a means for identifying when a patient is attempting to circumvent a dosing schedule for an inhalation device.

According to the invention, a control unit is either built-in or attached to an inhalation device. The control unit is either programmed or preset according to a prescribed dosing regimen for a particular drug to be administered. A timer is associated with the control unit and activates a signalling device if the patient does not actuate the inhalation device a programmed number of times within a preset time period at the prescribed dosing period. The timer/alarm combination may be set or programmed to sound the alarm a few minutes after the time period when the inhalation device is to be actuated, thereby allowing the patient to actuate the device in a timely manner without being subjected to an alarm signal.

A locking mechanism is preferably associated with the control unit and prevents the actuation of the inhalation device at non-prescribed intervals and prevents more than the prescribed number of doses to be administered at any particular dosing period. A recording device could be connected to the control unit so that the time and number of actuations of the inhalation could be recorded for later analysis. In addition, attempted actuations that were prevented by the locking mechanism could be recorded so that a patient's tendency towards dependency could be identified early in the treatment.

The inhalation device is also preferably equipped with a means for sensing if a patient is actually inhaling the medication. For example, a lip sensor at the inhalation device mouthpiece could be provided or a pressure transducer to sense the vacuum pressure created by patient inspiration could be provided. The means for sensing is connected to the control unit so that when a patient attempts to circumvent the dosing schedule by simply actuating the inhalation device without inhaling the drug, the attempt can be identified and the control unit can direct an alarm to be provided and that the event is recorded.

In a particular embodiment, the control unit is a module which includes a programmable chip or other circuitry. The chip could be programmed by the physician or by the inhalation device supplier to meet the dosing schedule for the drug to be delivered. In addition, the invention could advantageously use different computer chips which are preprogrammed for different times/doses for different drugs and different doses of a particular drug. The chips could be preset with a fixed time/dose schedule or they could be preset programmable where a pharmacist or physician sets the time/dose schedule. A patient's inhalation device could simply have a new chip plugged into the control module with the new drug prescription or with a new prescription of the same drug at higher or lower doses. In this way, the inhalation device could be reusable rather than disposable. In addition, the pluggable chip concept can benefit disposable inhalation device manufacture since the facility could make the same basic inhalation device for a variety of drugs, and this device would be modified prior to packaging by plugging in a suitable chip and drug filled canister. The chips could also be molded directly in the inhalation device body.

BRIEF DESCRIPTION OF THE DRAWINGS

The foregoing and other objects, aspects and advantages will be better understood from the following detailed description of a preferred embodiment of the invention with reference to the drawings, in which:

FIG. 1 is a cross-sectional view of a typical MDI;

FIG. 2 is a schematic drawing of the operational control members for this invention;

FIG. 3 is a flow chart showing the operational control according to this invention;

FIG. 4*a* is a cross-sectional side view of an MDI according to the invention which includes both a counting mechanism and an actuator mechanism;

FIG. 4*b* is a schematic drawing of an optical actuation sensing arrangement which could be used in the device of FIG. 4*a;* and FIG. 5 is a cross-sectional side view of a nebulizer device having an electronically controlled valve positioned in the air line prior to the formulation containment vessel.

DETAILED DESCRIPTION OF THE PREFERRED EMBODIMENTS OF THE INVENTION

As is explained in the co-pending patent application having Ser. No. 884,799, many drugs which are traditionally delivered by intravenous, subcutaneous, intramuscular, or intraperitoneal injection can advantageously be delivered by aerosol inhalation. Delivery of a drug to the alveoli in the lung to a point where the drug can pass through the lung mucosa can be accomplished with an MDI, nebulizer, dry powder inhaler, or like device which operates by a patient inspiring solubilized or micronized drug deep into the lung. In order for the drug to penetrate deeply in the lung, the particles containing the drug should be on the order of a few microns (0.2 to 20) in size. Aerosol delivery is particularly advantageous because first-pass metabolism of the drug by the liver and kidneys is avoided. In addition, the objectionable requirement of finding a suitable injection site and piercing the skin with a needle is avoided.

A wide variety of systemically active drugs would benefit from aerosol delivery via inhalation. For example, the delivery scheme would be useful for (1) neuroleptics, psychotropic drugs, and narcotic antagonists such as prochlorperazine, fluphenazine hydrochloride, and chlorpromazine, (2) antihistamines and immunotherapeutics including gammaglobulin, diphenyhydramine, chlorpheniramine, and pyribenzamine, as well as other immunosuppressives and immunomodulators (e.g., the recombinantly produced protein interferon alpha-2a), (3) tranquilizers, sedatives and analgesics such as dilaudid, demerol, and oxymorphone, (4) antibiotics such as penicillin, erythromycin, tetracycline, cephalothin, cefotaxime, carbenicillin, vancomycin, gentamycin, tobramycin, piperacillin, moxalactam, cefazolin, cefadroxil, cefoxitin, and amikacin, (5) cardiac drugs such as antihypertensives such as apresoline, atenolol, captopril, verapamil, enalapril, and antiarrhythmics including dopamine and dextroamphetamine, (6) antifungals including micozanole and amphotericin B, (7) secretory leukocyte protease inhibitor, (8) contraceptives such as norethindrone/ethinyl estradiol, norgesterol/ethinyl estradiol, and estrogen (can also be used to treat menopause and osteoporosis), (9) vaccines such as zidovudine and other HIV vaccines for AIDS, hepatitis B vaccine, herpes, malaria, measles, influenza, parainfluenza, adenovirus, rhinovirus, pertussis, and respiratory syncytial virus vaccines, (10) antiparasitic drugs such as pentamidine, (11) antiviral drugs such as acyclovir, azidothymidine, ganciclovor, enviroxime, ribavarin, rimantadine, and amantadine, (12) hormones such as insulin, oxytocin, calcitonin, human growth hormone, ACTH, LHRH, TSH, LH, estrogen, androgen, vasopressin and gonadotropin releasing hormone, (13) synthetic analogs of various hormones (e.g., leuprolide acetate is a nonapeptide analog of gonadotropin releasing hormone), (14) cytokines such as tumor necrosis factor (TNF), erythropoietin (EPO), interferons (IFN) (stimulate T lymphocytes to attack tumor tissue), colony stimulating factor (CSF), interleukins (IL)(regulate immune response), (15) polypeptides such as glucagon, atrial natriuretic factor and single chain antigen binding protein, (16) peptide growth factors such as epidermal growth factor (EGF), fibroblast growth factor (FGF), transforming (TGF), insulin-like growth factor (IGF), basic fibroblast (BF), and platelet derived growth factor (PDGF), (17) cardiovascular drugs (antihypertensives, antiarrhythmic and coronary vasodilators) including tissue plasminogen activator (TPA), platelet agonists to glycoproteins (e.g., GP IIb/IIIa), dehydroepiandrosterone (DHEA), platelet drugs and Factors VIIa, VIII, and IX, superoxide dismutase (SOD), atrial natriuretic factor (ANF), (18) monoclonal antibodies such as those available from Becton Dickinson/Immunex for treating graft v. host disease, those available from Bristol Myers Squibb for treating lung, colon, breast, and ovarian cancer, those available from Centocor for treating blood-clots, colorectal and pancreatic cancers, those available from Cetus for treating cancer and sepsis, those available from Chiron for treating septic shock, those available from Cutter Biological for treating pseudomonas infections and clinical sepsis, those available from Cytogen for treating ovarian, gastrointestinal, colorectal, and prostate cancers, those available from Lilly/Hybritech for treating various cancers, those available from Genetics Institute/NeoRx for treating colorectal cancer, those available from IDEC for treating B-cell lymphoma and malignant melanoma, those available from ImmunoGen for treating myeloid leukemias, B-cell leukemias and lymphomas, ex vivo autologous bone marrow and reinfusion for myelogenous leukemia, those available from Immunomedics for treating colorectal cancer, those available from Lederle for treating B-cell lymphoma, colon, breast, and lung cancers, those available from Ortho for treating heart and liver transplant rejection, those available from Pfizer/XOMA for treating gram-negative sepsis, and those available from XOMA for treating colorectal cancer, bone marrow transplantation graft vs host disease, type I diabetes, cutaneous T Cell lymphoma, inflammatory bowel disease, T-cell malignancy, and melanoma, (19) antisense (artificial DNA that causes complimentary RNA to self destruct), (20) DNase, (21) motion sickness, nausea, and vertigo drugs including meclizine and metoclopramide, (22) anticholinergic drugs (inhibitors) and antidotes, and (23) anticonvulsant, antispasmatic, and antisiezure drugs such as carbamazepine, and phenytoin drugs (e.g., Dilantin). The drugs could be purified from natural sources or recombinantly reproduced from bacterial cells, mammalian cells, insect cells, and plants.

As delivering systemic drugs by aerosol administration gains wider acceptance, there will be increased demands on the safety of inhalation devices. As is established by Spector, *Annals of Allergy*, 55:552–556 (1985), and Mawhinney et al., *Annals of Allergy*, 66:294–299 (1991), patient compliance with nebulizers and MDIs is not very good and many patients are not truthful about their drug usage. It is expected that with some drugs, relying on proper patient aerosol administration will not be acceptable. For example, with neuroleptics, psychotropics, narcotic antagonists, other central nervous system (CNS) drugs and headache analgesics, such as proclorperazine, fluphenazine hydrochloride, chlorpromazine, trifluperazine hydrochloride, thioridazine hydrochloride, loxapine hydrochloride, and haloperidol decanoate, anxiolytics such as alprazolam, busiprone and diazepam; antidepressants such as amitriptyline, clomipramine, doxepin and fluoxetine; antisomnatics such as flurazepam, temazepam and trizolam; anticonvulsants such as carbemazepine, phenytoin and clorazepam; antinausea drugs such as meclizine, metoclopramide, and prochlorperazine; anti-Parkinsoniam drugs such as levodopa, carbidopa, and selegiline; and migraine headache analgesics such as various butalbitol combinations, propanolol and nifedipine, there may be a tendency of some patients to overdose themselves. Overdosing may also be a problem with corticosteroids and some hormones.

Conversely, as is set forth in the Spector and Mawhinney et al. articles, underusage is a significant problem with prophylactic drugs (e.g., Lodaximide) which must be administered periodically over long periods of time. If treatments which require multiple doses over a long term treatment period are to be performed using an inhalation device as a delivery mechanism, efficacy will only result if the patient provides the requisite amount of drug during the treatment period.

This invention is specifically directed to providing inhalation devices, such as MDIs, nebulizers, and dry powder inhalers, with a safety alarm and actuator mechanism which both aids in assuring that a patient administers in a timely manner a required dose of drug and prevents overdosing a prescribed drug. For exemplary purposes only, the invention will be described in conjunction with an MDI. However, it should be understood that the same operational principles would also apply to nebulizers, dry powder inhalers, or other inhalation devices.

With particular reference to FIG. 1, there is shown a typical, prior art MDI comprised of a canister 10 filled with a drug and propellant mixture, positioned within a body comprised of the canister guide tube 12 and the mouth piece 14. The valve stem 16 is positioned within valve seat 18. Pressing down on the canister 10 will force the valve stem 16 into the canister 10, and a metering arrangement within the canister 10 will allow a precise amount of drug and propellant out through passage 19 and the spray jet 20 for inspiration by the patient. An air inlet port 22 allows ambient air into the MDI device.

This invention is particularly directed to providing the MDI or other inhalation device with both a means for notifying the patient when he or she should administer the drug and a means for preventing the patient from overdosing himself or herself with drug through either too many or too frequent actuations of the MDI.

Figure 2:
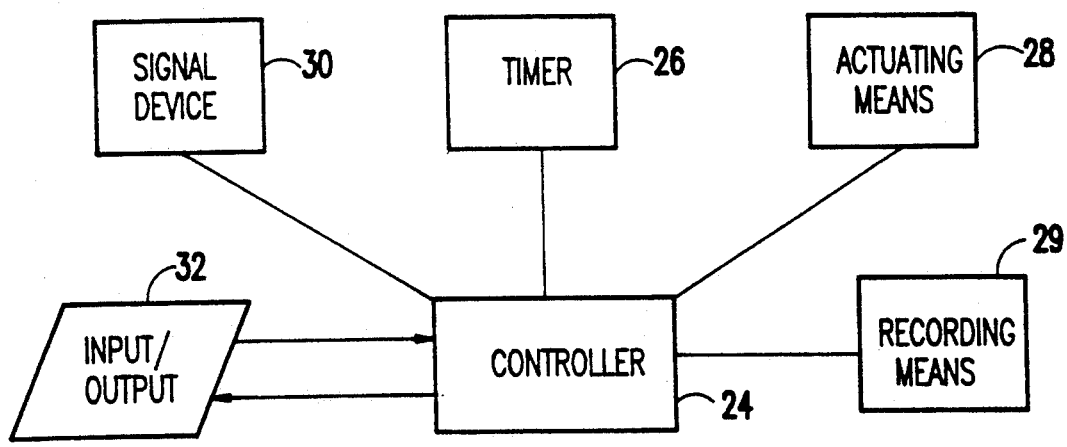

As is best shown in FIG. 2, the operational control of the MDI is accomplished with a controller 24 connected to a timer 26, actuating means 28, and signalling device 30. The controller 24 would ideally be either integral with or connected to the MDI and would have an automatic counter chip with a long-life miniature battery (e.g., nickel-cadmium or lithium, etc.). The timer 26, actuating means 28 and signalling device 30 could all be built-in or separate from the controller 24. In addition, a recorder 29 could be associated with or built-in the controller 24 so that a history of actuations and attempted non-prescribed actuations could be recorded for later analysis by the patient's physician.

The controller 24 could be an electronic device, a programmable device, or other suitable device. In a preferred embodiment, the controller 24 could be programmable or pre-programmed with the dosage information for the drug to be delivered by the MDI. Specifically, either the physician, pharmacist or drug manufacturer would input the number of actuations and time interval between actuations (e.g., two actuations every eight hours) into the controller 24 with input/output (I/O) device 32. The controller 24 would signal the actuator means 28 to lock-up and prevent actuation of the inhalation device after the requisite number of actuations have occurred and during the periods when actuation is not supposed to occur. For example, during a dose period, the controller 24 will sense two actuations and then will lock up and prevent actuation of the inhalation device until a predetermined minimal time has elapsed.

Programming the proper dosage schedule is well within the level of ordinary skill in the art and would be analogous to products like programmable pacemakers and programmable implantable pumps. In addition, pre-set electronic devices are well understood in the art and are applicable in the practice of this invention where an electronic chip 25 is inserted in the controller 24 to control the dosing/timing schedule. However, it should be understood that a major distinction between pacemakers and implantable pumps and inhalation devices is that the inhalation devices require patient interaction with the treatment supplying unit. With pacemakers and implantable pumps, the patient exercises no control over the treatment supplying unit. Therefore, the concept of dosing control in an inhalation device is a unique feature of this invention. It is anticipated that pre-set electronic devices or pre-programmed chips or programmable chips or the controller 24 containing these elements could be molded directly in the inhalation device body. In addition, the electronic devices or chips could be pre-set with the dosing schedule or could be settable or programmable with the dosing schedule by qualified medical personnel (e.g., Physician, Pharmacist, etc) or personnel at a pharmaceutical company which supplies the inhalation devices.

In a particular embodiment of the invention, the controller 24 would accommodate pluggable pre-programmed chips or other circuitry 25. The pluggable pre-programmed chips or other circuitry 25 would supply the dosing schedule for a particular aerosol formulation in canister 10. Hence, different pluggable chips 25 could be provided so that different timer/doses for different drugs and different doses of a particular drug could be accommodated by the same inhalation device. A patient's inhalation device would simply have a new chip 25 plugged into the controller 24 with the new drug prescription or with a new prescription of the same drug at higher or lower doses. In this way, the inhalation device could be reusable rather than disposable. In addition, the pluggable chip concept can benefit disposable inhalation device manufacture since the facility could make the same basic inhalation device for a variety of drugs, and this device would be modified prior to packaging by plugging in a suitable chip 25 and drug filled canister 10.

The actuator 28 could take a variety of forms. For example, the actuator 28 could be a valve that opens at preset time intervals and closes after a preset number of actuations, or a mechanical member which blocks the actuation of a canister in an MDI, etc. The timer 26 will monitor the time intervals between actuations so that the controller 24 can accurately control the actuator 28. The timer 26 will also monitor a time period during which dosing is to occur. In one embodiment, the timer 26 could cause the signalling device 30 to be activated at predetermined intervals dependent on the dosing schedule. In another embodiment, the signalling device 20 would only be activated if the patient does not take the prescribed doses within a preset time interval after his or her regularly scheduled dosing time. In this way, the user would not be subjected to what might be considered an annoying alarm if he or she is fairly compliant with the dosing schedule. In operation, if no actuation of the inhalation device occurs during a preset time period allocated for dosing, the controller 24 alerts the signalling device 30 to provide the patient with a signal to administer the drug. The signal provided by the signalling device 30 could be audible, visual, tactile, etc., or combinations thereof.

The number and time of actuations could be recorded by recording means 29. The recording means 29 could be a bubble memory, hysteresis memory, or other suitable memory device. The actuation information would then be downloaded to input/output unit 32 and printed off on a separate device (not shown) so the actuation history could be evaluated. Obviously, if the inhalation device were programmed at the factory, the input/output unit 32 would simply be sold to the physician as a downloading device. As will be explained below, the recording means 29 could also record information related to improperly attempted actuations (e.g., when a patient is trying to inhale more than the prescribed amount of drug by actuating the canister 10 additional times) and improperly performed actuations (e.g., when a patient actuates the device without inspiring). In this way, the recorded history could aid the physician in identifying the onset of addiction to certain prescribed drugs or a patient's psychological aversion to certain drug regimens.

Figure 3:
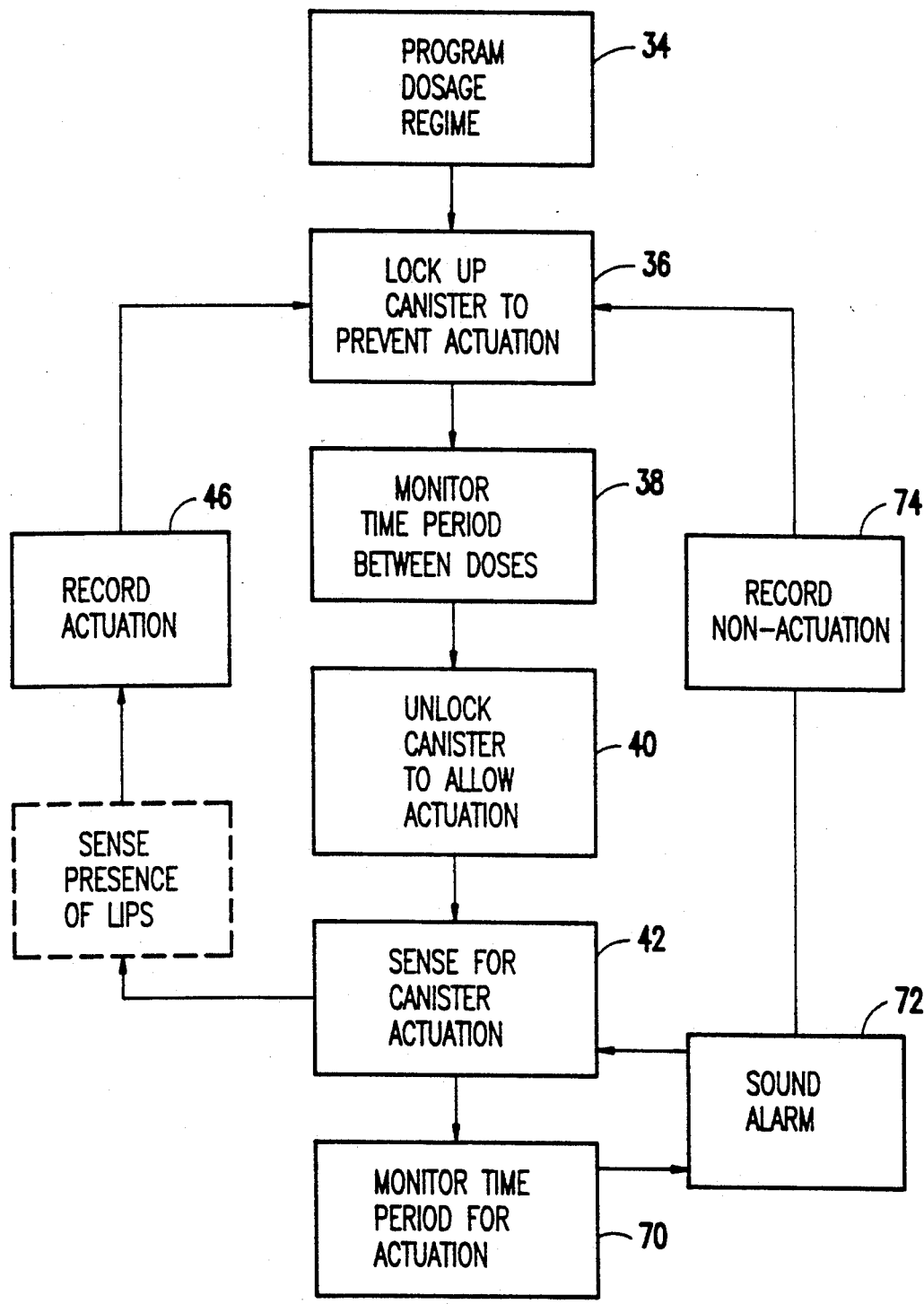

FIG. 3 shows the operation of the inhalation according to this invention. In step 34, the dosage regimen is programmed into the controller. The dosage regimen varies according to the drug being delivered, the patient being treated, and the inhalation device (MDI or nebulizer) being used. Programming the controller could be performed at the manufacturer's facilities for many prescription drugs. Rather than computer programming, preset electronic components could be used as the "programmed" dosage regime 34. In step 36, the operation of the inhalation device will be locked up until the preset dosing time. For example, the canister of an MDI could be prevented from being actuated during the non-dose periods. In step 38, the time period between doses is monitored. This is accomplished using a timer and the preprogrammed time period for dosing. In step 40, the inhalation device is permitted to be actuated for a preset interval once the preprogrammed time period for dosing arrives. This could be accomplished in an MDI by allowing the canister to move from its non-actuated position to its actuated position during the preset interval.

In step 42, actuation of the inhalation device is sensed and counted. A preferred sensing and counting mechanism similar to that which is disclosed in U.S. Pat. No. 5,020,527 to Dessertine, which is herein incorporated by reference, could be used. Specifically, as is shown in FIG. 4a where like numerals in FIG. 1 and 2 indicate like elements, the controller 24 would be positioned on guide tube 12, and a lever 44 or other element would extend into the MDI housing and be positioned for movement each time the canister 10 is pushed downwards. Movement of the lever 44 would actuate a microswitch on the controller 24 which would indicate that the canister 10 had been actuated.

Figure 4B:
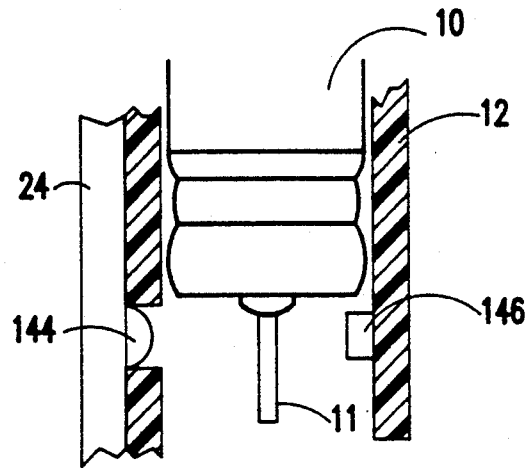
Figure 4A:
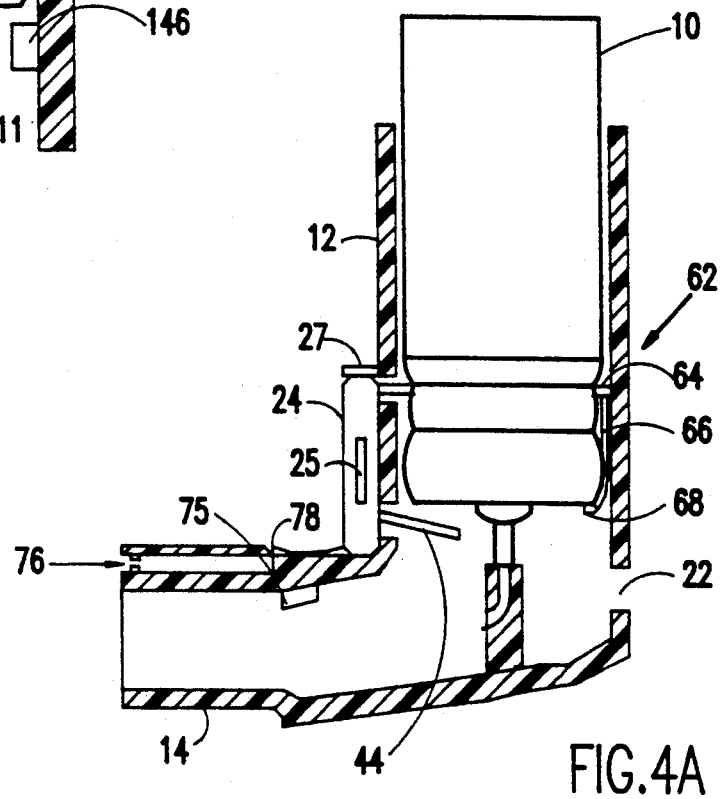

FIG. 4b shows an alternative actuation sensing arrangement wherein an optical sensor 144 monitors a spot or pattern 146 imprinted on guide tube 12. Each time a major portion of the canister 10 (e.g., more than stem 11) obstructs the optical sensor 144 image of the spot or pattern 146, as occurs when the canister 10 is depressed by the patient, a sensed actuation of the inhalation device is signalled to the controller 24.

With reference back to FIG. 3, the time and number of actuations of the inhalation device could be recorded at step 46. After the prescribed number of actuations occurs, operation of the inhalation device is again locked-up by returning to step 36 and no further actuations can be made until the prescribed interval between doses passes.

Figure 5:
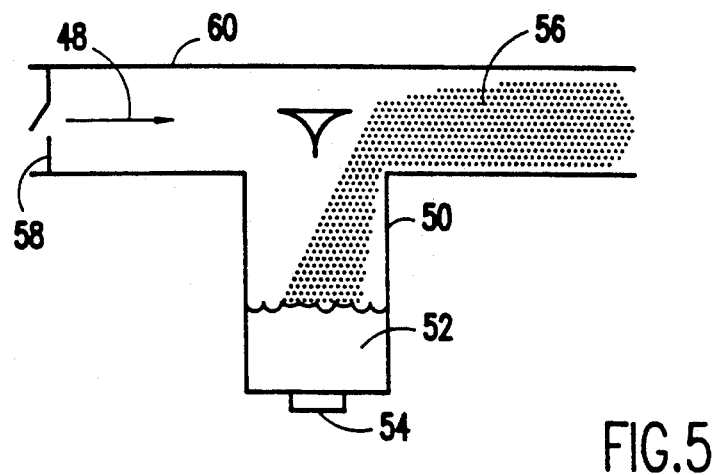

Locking up the inhalation device can be achieved by any number of means. For example, the controller 24 could operate a valve mechanism that prevents actuation of the inhalation device. This would be especially useful in nebulizers where a stream of air or other propellant is passed by an atomized nebulizer formulation to carry the drug to the patient. As is generally shown in FIG. 5, an air stream 48 is passed over the containment vessel 50 of a nebulizer device wherein a drug composition 52 positioned with in the containment vessel is atomized by a piezoelectric element 54 or other ultrasonic atomizing device such that the atomized drug 56 can be carried to the patient. By placing an electronically controlled valve 58 in the air or fluid line 60, the dispensing of drug can be effectively cut off at non-prescribed intervals and immediately after the prescribed dose has been administered.

FIG. 4b illustrates a lock up arrangement 62 which may be implemented on an MDI. Specifically, an arm 64 connected to the controller 24 selectively operates a pawl 66 which has an end 68 that engages the MDI canister 10 during periods when the canister 10 should not be actuated. A gear, ratchet, pivot, or other suitable arrangement allows the pawl 66 to swing to a non-engagement position during the period when dosing is to occur so that the canister 10 may move freely towards the valve seat 18 and supply a dose to a patient.

Other locking arrangements similar to those illustrated in FIGS. 4a and 4b could also be implemented.

To remind patients to administer the drug during the preset interval for dosing, the inhalation device is equipped with a signalling device (shown in FIG. 2). With reference to FIG. 3, step 70 provides a preset time period for actuation of the inhalation device during the time period programmed for dosing. In step 72, an alarm is provided to the patient to indicate that it is time to administer the drug. The alarm could be audible, visual, tactile, or any other suitable alarm. Audible alarms could be provided from a small speaker connected to the controller 24. Tactile alarms could be provided by a vibrating element connected to the controller 24. Similar alarm mechanisms can be found in the pager art which indicate when a person has received a phone call.

As is also shown in FIG. 3, the inhalation device can be set up so that if the patient administers a dose in a timely manner he or she will not be subjected to an alarm (something some patients might find annoying). Rather, the sensed actuation at step 42 would return the inhalation device to its locked up state of step 36. A two-stage signal could also be provided whereby a light 27 will become illuminated on the controller 24 at a prescribed dosing interval. If the patient retrieves the inhalation device during the prescribed dosing interval, illumination of the light 27 will provide assurance that the dosing time period has arrived. If the patient does not retrieve the inhalation during the prescribed dosing interval, the alarm, which would preferably be more noticeable to a patient such as an audible alarm or one that stimulates tactile receptors, would be signalled as is indicated in step 72 of FIG. 3.

Assuming the patient either actuates the inhalation device in a timely manner or responds to the alarm and actuates the inhalation device, the physical actuation of the inhalation device will be sensed at step 42 and the inhalation device will return to its locked up mode at step 36 to prevent further actuation. For example, if the required dose is two puffs, the device will lock up and prevent the patient from administering a third puff during the dosing interval. The time of actuation may be recorded in a memory (recording means 29) of the controller 24.

A time-out feature may be provided whereby after the time period for actuation at step 70, and after providing the alarm at step 72, the non-actuation of the device will be recorded at step 74 and the inhalation device will return to its locked up position at step 36. Alternatively, the alarm could continue to sound or vibrate until the inhalation device is actuated with the time for the next inhalation period being reset after the patient finally administers the prescribed drug dosage.

Upon the patient's check-up with the physician, the physician can down load the actuation and non-actuation information obtained at steps 46 and 74 and be provided with accurate history of the patient's usage of the inhalation device. The lever 44 shown in FIG. 4a, may also be positioned to actuate a secondary microswitch on the controller 24 when the patient attempts to improperly actuate the inhalation device. Actuation of the secondary microswitch would be accomplished by providing some "play" in the canister that allows for partial inward movement. Likewise, the optical sensor 144 could also sense a patient's attempts to improperly actuate the inhalation device. This would occur when the patient tries to administer too much drug and is prevented by the locking mechanism 64 (e.g., he or she attempts to administer additional drug at non-prescribed intervals or attempts to administer more than the prescribed dose at a dosing interval). By recording the number of improper attempts at actuating the inhalation device, the physician may derive some dosing frequency information which may be useful in counseling the patient or adjusting patient dose (e.g., lower doses more frequently administered).

An additional feature of this invention which aids in improving patient compliance is illustrated in FIG. 4a where a patient's attempts at circumventing a dosing schedule, as would occur if a patient actuated the device without inhaling any drug, are identified using a pressure transducer 75 and/or lip sensor arrangement. The pressure transducer 75 can sense whether there is any vacuum pressure being exerted on the inhalation device during actuation, as would be the case if the patient is inhaling drug. If no vacuum pressure is sensed coincident with the actuations, it is most likely that the patient is not inhaling the drug. The pressure transducer 75 would be electrically connected to the controller 24 so that the controller could direct the signalling device 30 to provide an alarm. The event could also be recorded on recording means 29. The lip sensor arrangement includes a pair of spaced apart electrical contacts 76 at the mouth piece 14 which are connected to the controller 24 by wire 78. When the patient presses the contacts 76 together with his mouth during actuation, delivery of the drug to the patient is confirmed. However, if the patient simply actuates the inhalation device without inspiring, the contacts 76 will not be connected and this situation will be sensed and recorded by controller 24. As described above, the condition of the contacts 76 may also be used to control the alarm sounded in step 72 (FIG. 3), whereby if the patient attempts to improperly actuate the inhalation device without inspiring, the alarm will be emitted.

It is also recognized that improper actuation of the inhalation device could occur accidentally (e.g., when a patient does not inhale properly). Therefore, the controller 24 could be programmed or pre-set to allow a manual override for a preset number of additional actuations. Other techniques for addressing this problem could also be implemented.

While the invention has been described in terms of its preferred embodiments, those skilled in the art will recognize that the invention can be practiced with modification within the spirit and scope of the appended claims.

Having thus described our invention, what we claim as new and desire to secure by Letters Patent is as follows:

1. A patient compliance system, comprising:
a drug delivery means;
a controller connected to said drug delivery means programmed or preset with dose and time of dose information for a drug being delivered by said drug delivery means, said dose and time of dose information setting forth a number of actuations of said drug delivery means to be provided at prescribed intervals;
a timer connected to said controller for tracking the time between actuations of said drug delivery means;
an actuator connected to said drug delivery means and said controller for actuating said drug delivery means, said actuator including means for preventing actuation of said drug delivery means when a patient attempts to actuate the drug delivery means at non-prescribed intervals or when a patient tries to exceed said number of actuations at said prescribed intervals;
means, coupled to said controller, for recording a time and number of actuations of said drug delivery means, said recording means being actuated by said actuator; and means for verifying that a patient is properly positioned to inhale drug from said drug delivery means, said verifying means comprising means for simultaneously sensing a patients mouth in close contact and around said drug delivery means, a drop in pressure in said drug delivery means and an actuation of said drug delivery means by said actuator.

2. A patient compliance system as recited in claim 1 further comprising a signalling device connected to said controller for signalling a prescribed interval for administration of said drug.

3. A patient compliance system as recited in claim 1 wherein said drug delivery means is a metered dose inhaler.

4. A patient compliance system as recited in claim 1 wherein said drug delivery means is a nebulizer.

5. A patient compliance system as recited in claim 1 wherein said drug delivery means is a powdered drug inhaler.

6. A patient compliance system as recited in claim 1 wherein said means for preventing actuation comprises locking means which includes a valve operated by said controller.

7. A patient compliance system as recited in claim 1 wherein said drug delivery means is a metered dose inhaler and wherein said actuator comprises a mechanical means for restraining a pressurized canister in said metered dose inhaler.

8. A patient compliance system as recited in claim 1 wherein said controller has a means for interacting with at least one of a plurality of interchangeable chips, each with different dose and time of dose information.

9. A patient compliance system according to claim 1, wherein said verifying means comprises means for sensing lips of a patient surrounding said drug delivery means and said lip sensing means is operable when said actuator is actuated by said patient.

10. A patient compliance system according to claim 9, wherein said lip sensing means comprises first and second electrical contacts coupled to said controller.

11. A patient compliance system according to claim 1, wherein said verifying means comprises a pressure transducer coupled to said controller and operable when said actuator is actuated by said patient.

12. A patient compliance system according to claim 1, wherein said verifying means comprises means for sensing lips of a patient surrounding said drug delivery means and a pressure transducer coupled to said controller and operable when said actuator is actuated by said patient, said verifying means being operable when said actuator is actuated by said patient.

13. A patient compliance system, comprising:
a drug delivery means;
a controller connected to said drug delivery means programmed or preset with dose and time of dose information for a drug being delivered by said drug delivery means, said dose and time of dose information setting forth a number of actuations of said drug delivery means to be provided at prescribed intervals;
a timer connected to said controller for tracking the time between actuations of said drug delivery means;
an actuator connected to said drug delivery means and said controller, said actuator preventing actuation of said drug delivery means when a patient attempts to actuate the drug delivery means at non-prescribed intervals or when a patient tries to exceed said number of actuations at said prescribed intervals;
means for recording a time and number of actuations of said drug delivery means, and
means for recording a time and number of attempted unprescribed actuations of said drug delivery means.

14. A patient compliance system, comprising:
a drug delivery means;
a controller connected to said drug delivery means programmed or preset with dose and time of dose information for a drug being delivered by said drug delivery means, said dose and time of dose information setting forth a number of actuations of said drug delivery means to be provided at prescribed intervals;
a timer connected to said controller for tracking the time between actuations of said drug delivery means;
an actuator connected to said drug delivery means and said controller for actuating said drug delivery means, said actuator including means for preventing actuation of said drug delivery means when a patient attempts to actuate the drug delivery means at non-prescribed intervals or when a patient tries to exceed said number of actuations at said prescribed intervals; and
means for recording a time and number of attempted unprescribed actuations of said drug delivery means.

15. A patient compliance system as recited in claim 14 further comprising a means for recording a time and number of actuations of said drug delivery means.

16. A patient compliance system as recited in claim 14 further comprising a means for verifying a patient is positioned properly to inhale drug from said drug delivery means.

* * * * *